United States Patent
Takahashi et al.

(10) Patent No.: US 8,556,875 B2
(45) Date of Patent: Oct. 15, 2013

(54) ABSORBENT LAMINATE AND DISPOSABLE ABSORBENT ARTICLE

(75) Inventors: Yuki Takahashi, Tsurugi-cho (JP); Akiko Tatsukawa, Tsurugi-cho (JP)

(73) Assignee: Livedo Corporation, Ehime (JP)

( * ) Notice: Subject to any disclaimer, the term of this patent is extended or adjusted under 35 U.S.C. 154(b) by 550 days.

(21) Appl. No.: 11/657,316

(22) Filed: Jan. 24, 2007

(65) Prior Publication Data

US 2007/0179469 A1 Aug. 2, 2007

(30) Foreign Application Priority Data

Jan. 30, 2006 (JP) ................. 2006-021214

(51) Int. Cl.
*A61F 13/15* (2006.01)

(52) U.S. Cl.
USPC .................... 604/385.101; 604/378

(58) Field of Classification Search
USPC .......................... 604/385.101, 378
See application file for complete search history.

(56) References Cited

U.S. PATENT DOCUMENTS

| | | | |
|---|---|---|---|
| 4,988,344 A * | 1/1991 | Reising et al. | 604/368 |
| 5,134,007 A | 7/1992 | Reising et al. | |
| 5,454,800 A * | 10/1995 | Hirt et al. | 604/378 |
| 5,855,572 A * | 1/1999 | Schmidt | 604/378 |
| 5,941,863 A * | 8/1999 | Guidotti et al. | 604/378 |
| 6,432,094 B1 | 8/2002 | Fujioka et al. | |
| 6,569,137 B2 | 5/2003 | Suzuki et al. | |
| 6,626,880 B2 * | 9/2003 | Onishi | 604/385.101 |
| 6,793,649 B1 | 9/2004 | Fujioka et al. | |
| 6,932,798 B2 * | 8/2005 | Kudo et al. | 604/385.01 |
| 6,965,058 B1 | 11/2005 | Raidel et al. | |
| 2006/0184146 A1 | 8/2006 | Suzuki | |

FOREIGN PATENT DOCUMENTS

| | | |
|---|---|---|
| CN | 1371671 | 10/2002 |
| EP | 0 316 771 | 11/1988 |
| EP | 0 804 915 | 11/1997 |
| EP | 0 958 802 | 11/1999 |
| EP | 1 609 448 | 12/2005 |
| JP | 11-332899 | 12/1999 |
| JP | 2003-070842 | 3/2003 |
| JP | 2003-70842 | 3/2003 |
| JP | 2004-130056 | 4/2004 |
| JP | 2005-006954 | 1/2005 |
| JP | 2005-296148 | 10/2005 |
| JP | 2005-307383 | 11/2005 |
| WO | WO-2004/084784 | 10/2004 |

OTHER PUBLICATIONS

Office Action from Chinese Patent App. No. 200710003673.2 (Dec. 29, 2011) with English translation thereof.

* cited by examiner

*Primary Examiner* — Lynne Anderson

(74) *Attorney, Agent, or Firm* — Cermak Nakajima LLP; Tomoko Nakajima

(57) ABSTRACT

The invention provides an absorbent laminate for absorbing a body fluid and usable for a disposable absorbent article, in which the absorbent laminate comprises an upper layer absorbent body and a lower layer absorbent body, the upper layer absorbent body has at least one opening part extended continuously or discontinuously in the longitudinal direction of the upper layer absorbent body, and the maximum width W1 of the opening part is 40% or less of the minimum width W2 of the upper layer absorbent body. The invention also provides a disposable absorbent article provided with the absorbent laminate.

17 Claims, 5 Drawing Sheets

ABSORBENT LAMINATE AND DISPOSABLE ABSORBENT ARTICLE

FIELD OF THE INVENTION

The invention relates to an absorbent laminate that hardly causes deformation and is highly effective to prevent urine leakage, and a disposable absorbent article such as disposable diapers or disposable pants comprising the absorbent laminate.

BACKGROUND OF THE INVENTION

An absorbent body to be used for disposable diapers or disposable pants is generally formed by mixing pulp fibers (cotton-like crushed pulp), thermofusible fibers, highly water absorbent resin powder, and the like pneumatically sent from respective storage tanks and sucking and depositing the mixture to and on the circumferential face of a suction drum formed a recessed part (a suction region) with an approximately same shape of that of an aimed absorbent body. The absorbent deposited on the suction drum by suction is transferred to a suction conveyer for transportation and assembled in a production line of the disposable absorbent article.

Herein, in the case where the absorbent body is a double layer structure, a method which includes arranging two suction drums in series, synchronously controlling the drums, and layering an upper layer absorbent body formed on the downstream side suction drum on a lower layer absorbent body transferred to a suction conveyer from the upstream side suction drum, is employed.

Conventionally, many absorbent bodies with a double layer structure have had a structure with a projected cross-sectional shape formed by layering the upper layer absorbent body with a smaller surface area than that of the lower layer absorbent body on the center of the lower layer absorbent body to increase the absorption amount of urine or the like or to improve the close fitting to the crotch of a female. However, an absorbent body with such a structure thick in the center part is hard to be twisted along the movement of the wearer and consequently sometimes forms a gap from an excretory organ. Further, in the case of using it in combination with a urine removal pad, the volume becomes further bulky and it results in unpleasant stiff feeling for the wearer.

To solve the above-mentioned problem, the applicant of this invention found an absorbent laminate with a simple structure that was easy to be twisted along the body shape and movement of the person who put it on and effective to prevent leakage without giving stiff impression to the person who put it on even in the case where the absorbent laminate was used in combination with a separate urine removal pad and already applied for a patent (Japanese Patent Application Laid-Open (JP-A) No. 2003-70842).

DISCLOSURE OF THE INVENTION

Problems to be Solved by the Invention

The absorbent laminate disclosed in the above-mentioned JP-A No. 2003-70842 is formed by layering upper and lower two-layers of absorbent webs comprising pulp fibers and highly water-absorbent resin powder dispersed therein and the upper layer absorbent web is provided with at least one opening part with a smaller surface area than that of the lower layer absorbent web at the arrangement position of the lower layer absorbent web and set more dispersion density of the highly water-absorbent resin powder in the surrounding of the opening part than in other portions. Formation of the opening part with a relative large size enables the absorbent laminate to be twisted easily and follows the movement of the wearer to prevent leakage. Further, since the volume is prevented from becoming bulky in the crotch part even if a separate urine removal pad is layered, no stiff impression is given to the wearer. Further, since the dispersion density of the highly water-absorbent resin powder is increased in the surrounding of the opening part, the leakage prevention effect is efficiently caused.

However, in order to further improve absorbent capacity, if the dispersion density of the highly water-absorbent resin powder is increased in the entire absorbent laminate, it is necessary to increase more the dispersion density of the highly water-absorbent resin powder in the surrounding of the opening part and consequently, there is a problem that lessens a relative amount of the pulp fibers in the periphery of the opening part to make the absorbent web easy to deform. Further, if the dispersion density of the highly water-absorbent resin powder is increased, the relative amount of the pulp fibers is lessened also in the entire upper layer absorbent web in combination with the large size opening part, there is a problem that is easy to deform the entire upper layer absorbent web.

Therefore, it is an object of the present invention to provide a disposable absorbent article provided with an absorbent effective to prevent leakage, hard to be deformed, and sufficient in water absorption capability.

Means for Solving the Problems

The present invention for solving the above-mentioned problems gives an absorbent laminate for absorbing a body fluid and usable for a disposable absorbent article, wherein the absorbent laminate comprises an upper layer absorbent body and a lower layer absorbent body, the upper layer absorbent body has at least one opening part extended continuously or discontinuously in the longitudinal direction of the upper layer absorbent body, and the maximum width W1 of the opening part is 40% or less of the minimum width W2 of the upper layer absorbent body.

Since the long narrow opening part with the maximum width W1 at 40% or less of the minimum width W2 of the upper layer absorbent body is formed in the upper layer absorbent body of the absorbent laminate, even if the absorbent body is twisted because of power application inward in the crotch of the wearer, the opening part is closed and prevents formation of irregular gathers and projections and recessions in the absorbent laminate to keep the absorbent body flat. Consequently, deformation of the absorbent laminate is prevented and the close fitting of the body to the cloth of the wearer is improved to further improve the leakage prevention effect. On the other hand, when the opening part is not closed, since the diffusion of a body fluid in the longitudinal direction of the absorbent body is promoted, the absorbent capability of the lower layer absorbent body is sufficiently exhibited.

DESCRIPTION OF THE PREFERRED EMBODIMENT

The present invention gives an absorbent laminate for absorbing a body fluid and usable for a disposable absorbent article, wherein the absorbent laminate comprises an upper layer absorbent body and a lower layer absorbent body, the upper layer absorbent body has at least one opening part extended continuously or discontinuously in the longitudinal direction of the upper layer absorbent body, and the maximum width W1 of the opening part is 40% or less of the minimum width W2 of the upper layer absorbent body.

It is preferable that the upper layer absorbent body and the lower layer absorbent body are respectively made of fiber aggregates containing 20% by weight or more of highly water-absorbent resin powder. Sufficiently high water absorption capacity can be secured and reversion of a liquid is scarcely caused.

The upper layer absorbent body may have a configuration having two or more opening parts which are arranged right and left symmetrically on both side of the center line along the longitudinal direction of the upper layer absorbent body and have fiber aggregates exist on the center line. The opening part may be arranged unevenly in the edge side along either one of the width directions of the upper layer absorbent body. If a filament nonwoven is laid as a liquid-permeable intermediate sheet at least beneath the opening part between the upper layer absorbent body and the lower layer absorbent body and the liquid-permeable intermediate sheet is bonded to one or both of the upper layer absorbent body and the lower layer absorbent body, the deformation of the upper layer absorbent body is further efficiently prevented. If the liquid-permeable intermediate sheet is colored with a color other than white color, the position of the opening part is easy to be seen and therefore it is preferable.

The invention includes a disposable absorbent article provided with the absorbent laminate. The disposable absorbent article includes disposable diapers, disposable pants, incontinence pads, sanitary napkins, sanitary shorts, and the like.

Figure 1:
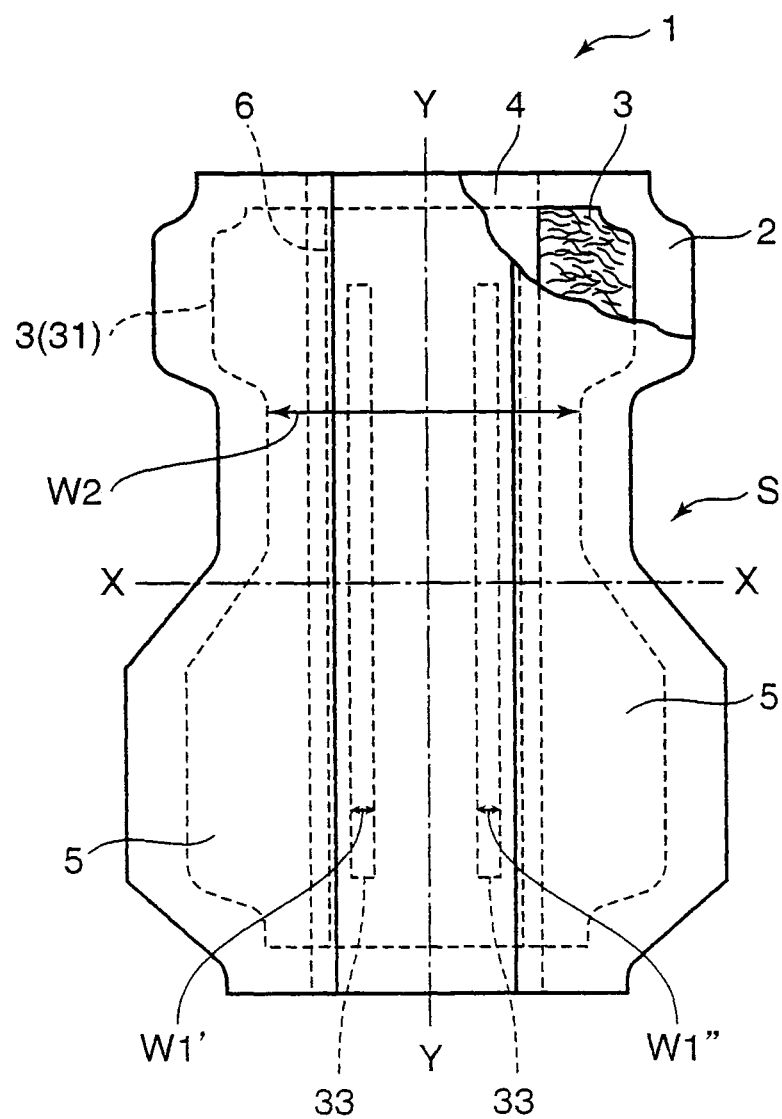
FIG. 1 shows a plane view of a disposable auxiliary pad using a representative absorbent laminate of the invention with portions cut away.
Figure 2:
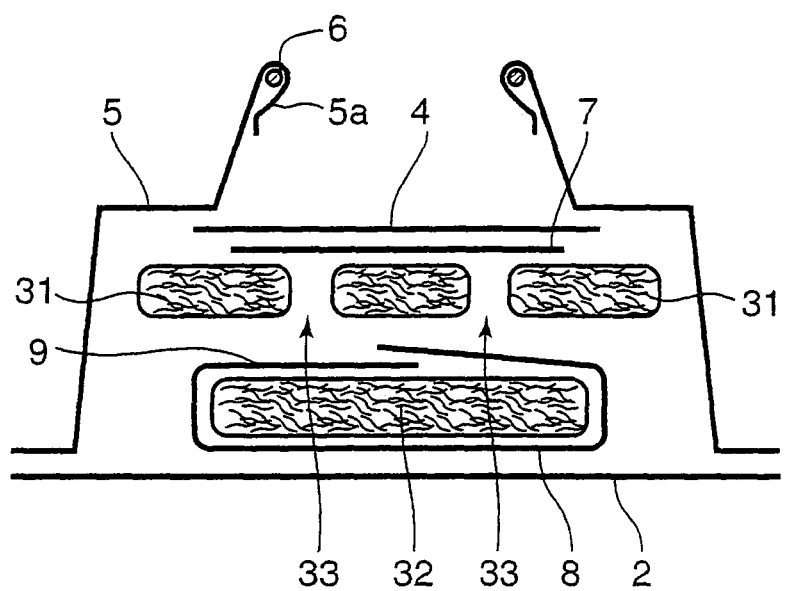
FIG. 2 shows a schematic cross-sectional view along X-X line in FIG. 1.

FIG. 1 shows a plane view of a disposable auxiliary pad using a representative absorbent laminate of the invention. FIG. 2 shows a schematic cross-sectional view along X-X line in FIG. 1. In this cross-sectional view, the respective constituent components are shown apart for easy understanding. The disposable auxiliary pad 1 basically comprises a back sheet 2, an absorbent laminate 3, a top sheet 4 with a narrower width than that of the back sheet, and a pair of right and left side sheets 5. The X-X line is the center line (the longitudinal direction center line) along the width direction and the Y-Y line is the center line (the width direction center line) along the longitudinal direction and the upstream side of the X-X line is set to be the front and the downstream side of the X-X line is set to be the rear.

The back sheet 2 is made of a synthetic filament nonwoven having an approximately sand glass-like shape and water-repelling property, a synthetic resin film of polyethylene or the like (preferably a liquid-impermeable and breathable film), or a laminate of them, and leg hole parts S are formed in both sides in the crotch portion. The back sheet 2 may have a simple rectangular shape. The nonwoven may be made of synthetic fibers such as polypropylene, polyethylene, polyester, or nylon; and composite fibers made of combinations of polyester/polyester, polyester/polyethylene, polypropylene/polyethylene and the like. The nonwoven is preferably produced by solely a spunbond method, an air through method, a point bond method, a melt blowing method, or an air laid method or a method of combining a plurality of these methods. Especially, a filament nonwoven produced by the spunbond method or a SMS method in which the spunbond method and the melt blow method are combined is preferable in terms of the strength. The filament nonwoven produced by the spunbond method is most preferable.

The top sheet 4 may be made of a nonwoven or a woven fabric made of synthetic fibers having liquid-permeability and be formed in a rectangular shape with a narrower width than that of the top sheet 2 and the same length as that of the top sheet 2. The down face of the top sheet 4 and the upper face of the back sheet 2 are bonded in the state that the absorbent laminate 3 is inserted between them. Hydrophilic fibers such as silk, rayon, pulp, or the like and the above-exemplified fibers or composite fibers are preferable to be used for the nonwoven or the woven fabric, and in order to increase the liquid permeability, the fibers or the nonwoven or the woven fabric may be subjected to treatment for hydrophilicity.

The pair of the right and left side sheets 5 may be made of a synthetic fiber nonwoven having water repelling property and have approximately same length as those of the back sheet 2 and the top sheet 4 and width sufficient to cover from the inside of the outside edge of the top sheet 4 to the side edge of the back sheet 2 and leg hole parts S with the same shape as that of the back sheet 2 are formed. The overlapping portions of the respective side sheets 5 on the top sheet 4 are bonded to the top sheet 4 and the externally extended parts extended to the outside of the top sheet 4 are bonded to the back sheet 2.

Inside edges 5a of the respective side sheets 5 are folded downward to the inside, and along the entire length of the respective side sheets 5, elastic threads 6 for three-dimensional gathers are attached into the folded portions in the elongated state. The inside edges 5a of the side sheets 5 are bonded to the top sheet 4 in the front and rear ends of the disposable auxiliary pad 1 and construction of the elastic threads 6 for three-dimensional gathers raises the inside edges 5a in a manner that the right and left upper faces of the upper layer absorbent body 31 of the absorbent laminate 3 are being covered and thus prevents transverse leakage of urine or the like.

The absorbent laminate 3 comprises the upper layer absorbent body 31 having the opening parts 33 and 33 with a long narrow rectangular shape extended continuously in the longitudinal direction and the lower layer absorbent body 32. The upper layer absorbent body 31 has a sandglass-like shape one size smaller than that of the back sheet 2 and the lower layer absorbent body 32 is formed into an approximately rectangular flat shape with the approximately same width as that of the top sheet 4. In the drawing, the opening parts 33 and 33 are arranged symmetrically on both side of the Y-Y line and the fiber aggregates exist on the Y-Y line. An upper layer sheet 7 is inserted between the upper layer absorbent body 31 and the top sheet 4. In the lower layer absorbent body 32, a lower layer sheet 8 is curled up to the top face of the lower layer absorbent body 32 from both end side parts and layered in a manner that the lower layer absorbent body 32 is wrapped with the lower layer sheet 8. As a result, the lower layer sheet 8 on the top face of the lower layer absorbent body 32 works also as a liquid-permeable intermediate sheet 9. As described, the upper layer absorbent body 31 is put between the upper layer sheet 7 and the liquid-permeable intermediate sheet 9, so that the upper layer absorbent body 31 can have a structure further hard to be deformed. The lower layer absorbent body 32 is also made to have structure hard to be deformed since it is wrapped with the lower layer sheet 8. If one or both of the upper and lower layer sheets 7 and 8 and one or both of the upper and lower layer absorbent bodies 31 and 32 are bonded with a hot melt adhesive or the like, the strength of the absorbent laminate 3 is further improved and therefore, neither deformation nor breakage is caused even if the absorbent laminate 3 is twisted.

If the portion of the liquid-permeable intermediate sheet 9 of the lower layer sheet 8 is colored with a color other than white, which is a color of the nonwoven, even if the top sheet 4 and the upper layer sheet 7 exist, the color of the liquid-permeable intermediate sheet 9 under the opening parts 33 can be seen from the upper side and the wearer can know the positions of the opening parts 33 and therefore it is preferable. If the opening parts 33 are visible, they can work as a mark at the time of putting the absorbent laminate to the crotch of the person who uses it or at the time of using another absorbent article such as a disposable auxiliary pad and thus it improves the convenience for the person who put it on or a care taker. The color of the liquid-permeable intermediate sheet 9 is preferably colors other than red, yellow, or brown and preferably, for example, pale green or pale blue.

The upper and lower layer sheets 7 and 8 may be hydrophilic or liquid-permeable sheet materials such as tissue paper (thin paper) and a liquid-permeable nonwoven. In the case of the liquid-permeable nonwoven, liquid-permeable nonwoven with metsuke (mass per unit area) of about 10 to 30 g/m$^2$ (particularly polypropylene nonwoven produced by a spunbond method) are preferable and in the case of tissue paper, metsuke (mass per unit area) of about 10 to 30 g/m$^2$ is also preferable. The liquid-permeable intermediate sheet 9 may be formed by inserting another sheet between the upper and lower layer absorbent bodies 31 and 32 without using a portion of the lower layer sheet 8 and in the case of such a configuration, it is preferable to use the above-mentioned nonwoven for the liquid-permeable intermediate sheet 9 and tissue paper for the upper and lower layer sheets 7 and 8. In the absorbent laminate 3, the lower layer absorbent body 32 is bonded to the upper face of the back sheet 2 in a manner that the lower layer absorbent body 32 is set downward.

The maximum width W1 of the opening part 33 is adjusted to be at 40% or less of the minimum width W2 of the upper layer absorbent body 31 in terms of the prevention of deformation of the upper layer absorbent body 31. It is more preferably 30% or less and even more preferably 20% or less. To cause the effect of the opening part formation, the lower limit of the maximum width W1 of the opening part is preferably 4%. The maximum width W1 of the opening part is defined as the maximum length in the case where the opening part extended in the longitudinal direction of the upper layer absorbent body 31 is cut off along the single line parallel to the X-X line. Accordingly, in FIG. 1, the maximum width W1 of the opening part 33 is the total of the width of the right and left opening parts 33 (the sum of W1' and W1" in FIG. 1).

Figure 3:
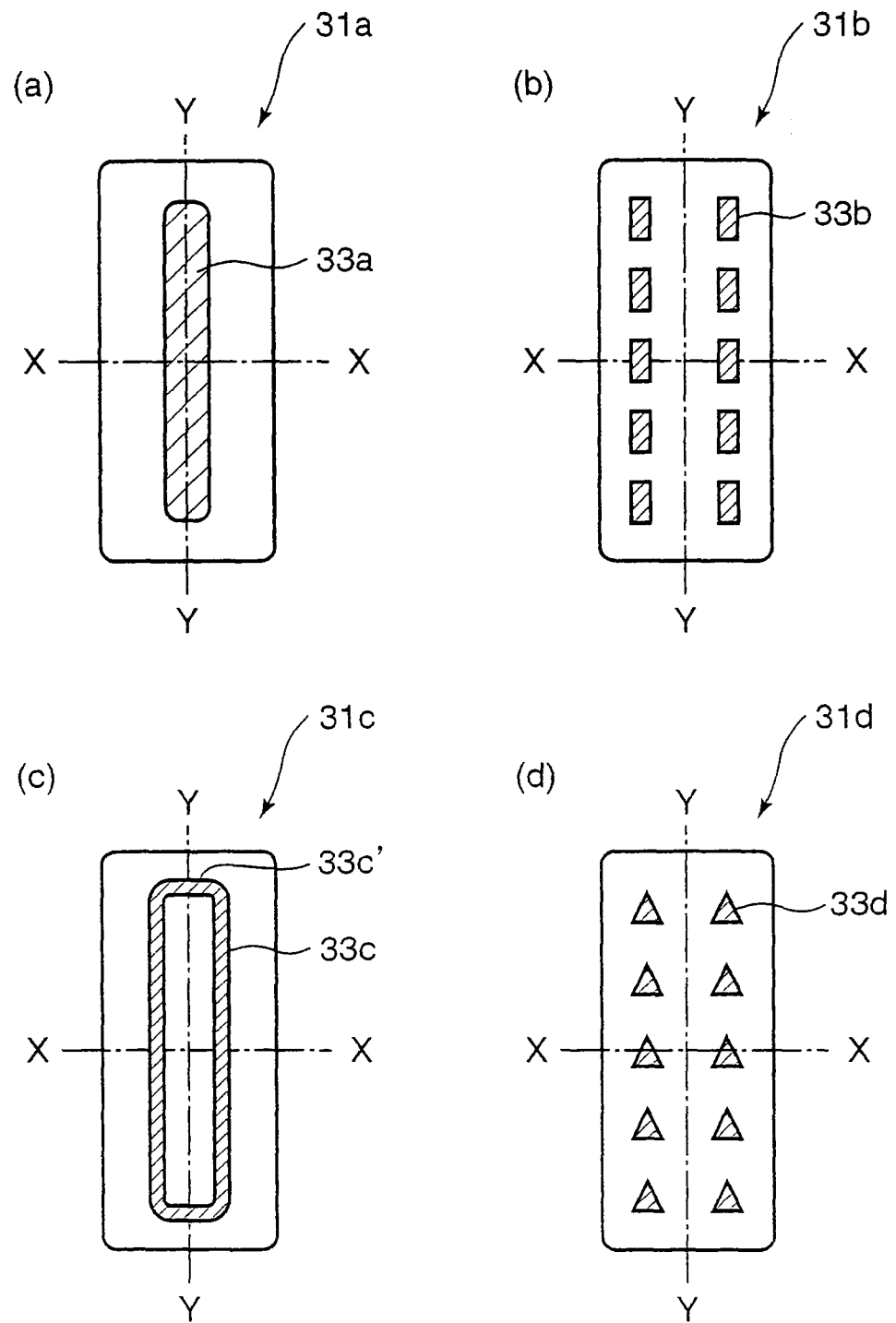
FIGS. 3A to 3D show plane views of the upper layer absorbent body having opening parts with different shapes.

FIG. 3 shows a plane view of the upper layer absorbent body 31 having opening parts with another shape in a different positioning relation. FIG. 3A shows an example of a rectangular upper layer absorbent body 31 having one opening part 33a extended in the longitudinal direction in the center region. FIG. 3B shows an example of a rectangular upper layer absorbent body 31 having small rectangular opening parts 33b extended discontinuously in the longitudinal direction of the upper layer absorbent body 31. The opening parts 33b are arranged symmetrically on both side of the Y-Y line and fiber aggregates exist on the Y-Y line. FIG. 3C shows the arrangement of long narrow ring-like opening part 33c extended continuously in the longitudinal direction of the upper layer absorbent body 31. The opening parts 33c are arranged symmetrically on both side of the Y-Y line and fiber aggregates exist on the Y-Y line. FIG. 3D shows the arrangement of small triangular opening parts 33d extended discontinuously in the longitudinal direction of the upper layer absorbent body 31. The opening parts 33d are also arranged symmetrically on both side of the Y-Y line and fiber aggregates exist on the Y-Y line.

Since the opening parts 33a to 33d shown in FIG. 3 are extended in the longitudinal direction of the upper layer absorbent body 31, they are highly effective to diffuse a body fluid in the longitudinal direction and absorb the body fluid in the lower layer absorbent body 32. Further, with respect to the upper layer absorbent bodies 31b to 31d of FIGS. 3B to 3D, the fiber aggregates exist on the Y-Y line, so that the close fitting to the crotch of the wearer can be improved and a body fluid can be quickly absorbed in the absorbent laminate 3 to efficiently prevent the leakage. Further, since the opening parts shown in the drawings have long narrow shapes, even if the absorbent body is twisted because of power application inward in the crotch of the wearer, the opening parts are closed and prevent formation of irregular gathers and projections and recessions in the absorbent laminate 3 and accordingly, the upper face of the upper layer absorbent body 31 can be kept flat. Since arrangement of the opening parts is made symmetrical on a line, the effect to keep the upper face of the upper layer absorbent body 31 can be further improved. Consequently, deformation of the absorbent laminate 3 is prevented and the close fitting of the body to the cloth of the wearer is improved to further improve the leakage prevention effect.

As described above, the maximum width W1 of the opening part is defined as the maximum length in the case where the opening part extended in the longitudinal direction of the upper layer absorbent body 31 is cut off along the single line parallel to the X-X line. As shown in FIG. 3C, in the case where there are opening parts 33c' extended in the width direction of the upper layer absorbent body 31, the maximum width W1 is determined in a manner that the line parallel to the X-X line does not pass that portions. In the case of FIG. 3A, the maximum width W1 of the opening part is the length of the short side of the rectangular opening part 33a: in the case of FIG. 3B, the maximum width W1 of the opening part is the length two times as long as the short side of the rectangular opening part 33b: in the case of FIG. 3C, the maximum width is the length two times as long as the groove width of the ring-like opening part 33c: and in the case of FIG. 3D, the maximum width is the length two times as long as the length of the bottom side of the triangle. As long as the maximum width W1 of the opening part is 40% or less of the minimum width W2 of the upper layer absorbent body 31, the number of the lines of the opening parts may be three or more.

The upper layer absorbent body 31 and lower layer absorbent body 32 are preferable to have a configuration of fiber aggregates containing fibers and highly water-absorbent resin powder. The fibers to be used may be mainly fibrillated pulp fibers and cellulose fibers and if necessary thermofusible fibers may be mixed. The highly water-absorbent resin powder is added preferably in an amount of 20% by weight or higher in 100% by weight of the total amount of the fibers and the highly water-absorbent resin powder. It is because if 20% by weight or more of the highly water-absorbent resin powder is added to the upper and lower layer absorbent bodies, the water absorption capability can be improved. Further, reversion of the excreted liquid can be prevented by keeping the liquid in the highly water-absorbent resin powder. However, if the highly water-absorbent resin powder is added so much, the upper and lower layer absorbent bodies 31 and 32 become stiff and therefore, the addition amount is preferably 80% by weight or less and more preferably 60% by weight or less. As the highly water-absorbent resin powder are poly(acrylic acid) (salt) powders, which are used commonly in this field, preferable.

The absorbent laminate 3 shown above is made to have a structure in which the lower layer absorbent body 32 is made narrower in the width than the upper layer absorbent body 31 and both end parts in the longitudinal direction of the upper layer absorbent body 31 are extended outwardly from both end parts in the longitudinal direction of the lower layer absorbent body 32. Of course, both absorbent bodies 31 and 32 may have the same width and both end parts in the longitudinal direction of the upper layer absorbent body 31 may be conformed to both end parts in the longitudinal direction of the lower layer absorbent body 32.

Figure 4:
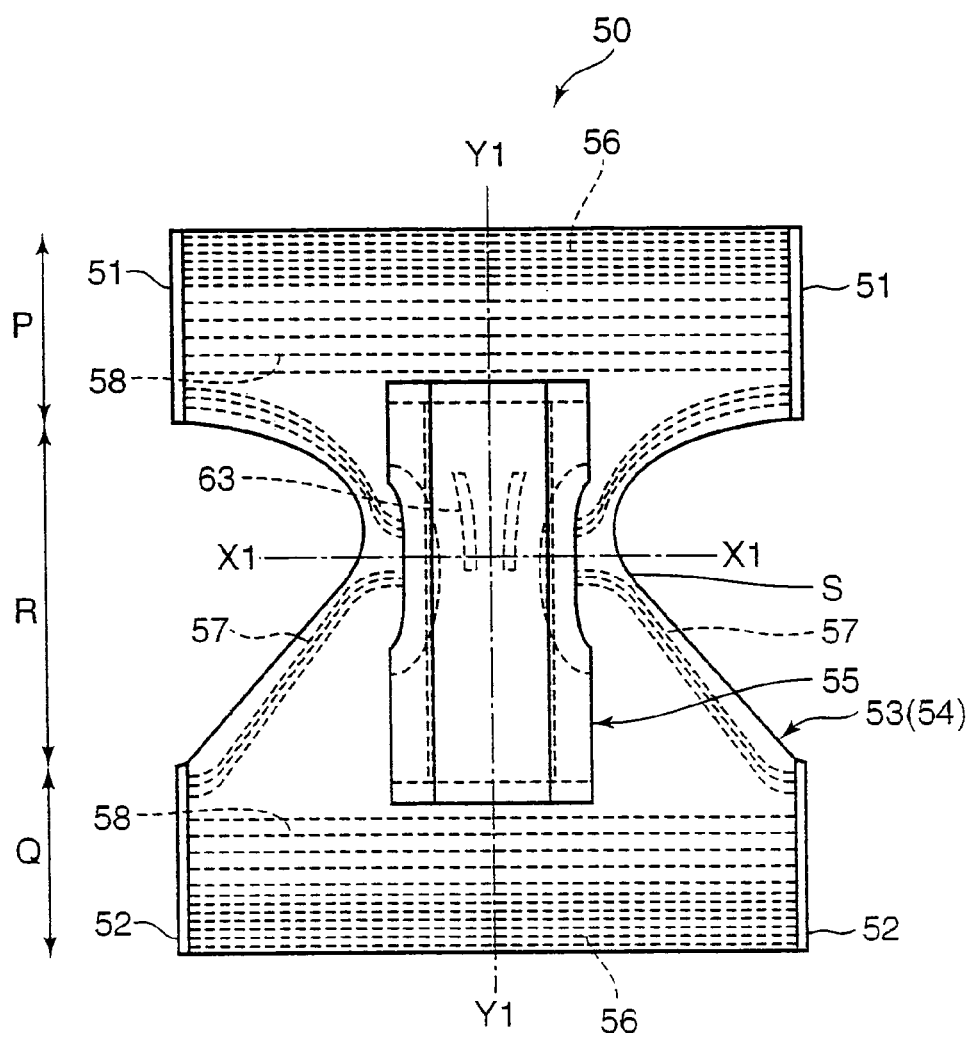
FIG. 4 shows a plane view of the development of disposable pants using a representative absorbent laminate of the invention.
Figure 5:
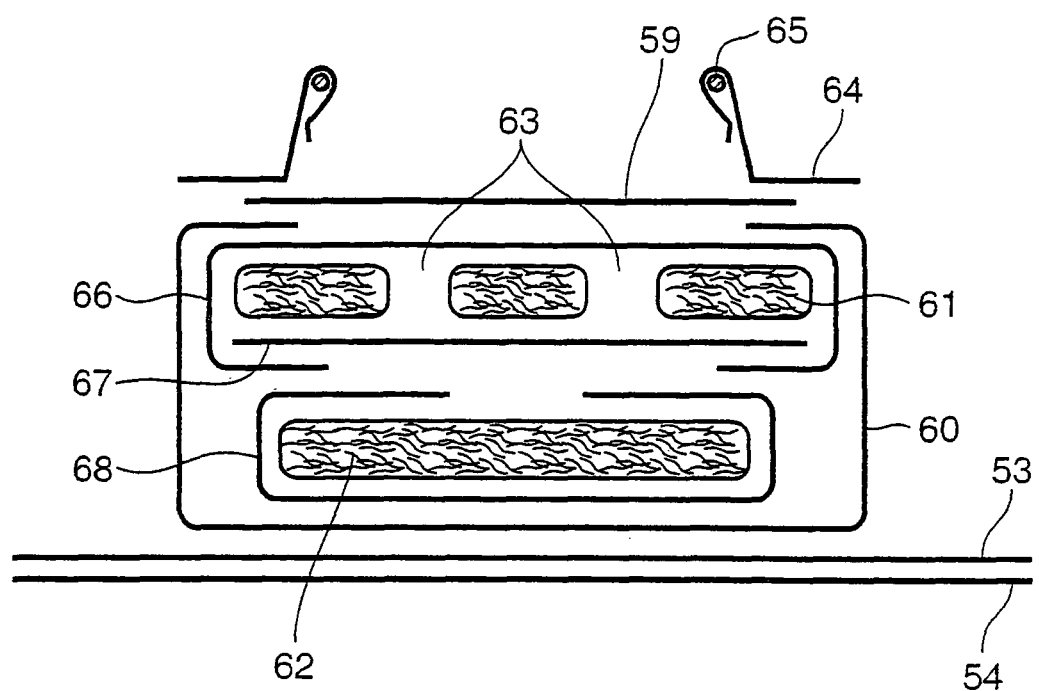
FIG. 5 shows a schematic cross-sectional view along X1-X1 line in FIG. 4.

FIG. 4 shows a development of disposable pants 50, which is another embodiment of a disposable absorbent article of the invention. FIG. 5 shows a cross-sectional view of the disposable pants shown in FIG. 4 along the X1-X1 line. The disposable pants 50 have a front belly part P, a rear back part Q, and a crotch part R and leg hole parts S are formed in the crotch part R. The disposable pants 50 is formed to have a waist opening and a pair of the right and left leg hole parts S by bonding the right and left side edge parts 51 of the front belly part P to the right and left side edge parts 52 of the rear back part Q, respectively. The disposable pants 50 basically has a configuration composed of the outer member 53 (54) with the appearance of pants and an absorbent main member containing the absorbent laminate 55 of the invention capable of containing and holding a body fluid in the inner face of the outer member. A user can use the pants by inserting the legs through the waist opening toward the right and left leg hole parts and thus putting the pants on.

An elastic thread 56 for waist is attached in the waist circumference direction to the waist opening part of the disposable pants 50 while being stretched. An elastic thread 57 for legs is attached to the circumferential edges of the leg holes while being stretched. Further, an elastic thread 58 for trunk circumferences is attached in the trunk circumferential direction to the trunk circumferential part between the waist opening and the leg hole parts S while being stretched. The disposable pants 50 is well fitted to the wearer by contraction of the elastic thread 56 for waists, the elastic thread 57 for trunk circumferences, and the elastic thread 58 for legs.

The absorbent laminate 55 of the disposable pants 50 comprises an upper layer absorbent body 61 and a lower layer absorbent body 62 sandwiched and bonded between a liquid-permeable top sheet 59 and a liquid-permeable back sheet 60. Long narrow opening parts 63 extended in the longitudinal direction of the upper layer absorbent body 61 are arranged at two positions symmetrically on both side of the Y1-Y1-line in the upper layer absorbent body 61. The opening parts 63 are arranged unevenly toward the front belly part P crossing the X1-X1 line and slightly curved toward the inside of the disposable pants 50. Since the opening parts 63 are arranged unevenly toward the front belly part P, the surface area of the absorbent laminate 55 is assured to be wide from the crotch part R to the rear back part Q. Further, the effect of the long narrow opening parts is as described above.

In this example, the back sheet 60 is curled up to the upper face of the upper layer absorbent body 61. In both right and left edge parts of the top sheet 59, side sheets 64 are bonded to the top sheet 59 and the upper face of the curled back sheet 60. An elastic thread 65 for three-dimensional gathers is attached to the side edges of the side sheet 64 while being stretched and lateral leakage of a body fluid such as urine or the like can be prevented by forming the three-dimensional gathers rising upward by contraction of the elastic thread 65.

In this example, the upper layer sheet 66 of the upper layer absorbent body 61 is folded downward to the lower side of the upper layer absorbent body 61 and a liquid-permeable intermediate sheet 67 is inserted between the folded face of the upper layer sheet 66 and the lower end of the upper layer absorbent body 61. The lower layer sheet 68 is folded upward from both side parts of the lower layer absorbent body 62 to the upper face of the lower layer absorbent body 62. These constituent members may be bonded properly using a hot melt adhesive. The materials usable for the respective members are same as those for the case of the above-mentioned absorbent laminate 3.

The outer member is composed of two sheets 53 and 54 and the above-mentioned elastic thread 56 for waists, the elastic thread 57 for trunk circumferences, and the elastic thread 58 for legs are attached between them while being stretched. A water-repelling nonwoven or a liquid-impermeable plastic film may be used for the sheets 53 and 54 composing the outer member, however to prevent dampening, the water-repelling nonwoven is preferable.

Elastic stretchable materials (polyurethane threads, natural rubber) frequently used for disposable absorbent articles are preferable for the elastic threads to be used for the invention. String-like polyurethane films may be also usable. While being stretched, the elastic threads are attached by preferable means such as a hot melt adhesive, heat adhesion, ultrasonic adhesion, or the like. It is preferable to attach a polyurethane thread with a fineness of 300 to 2000 dtex while stretching the thread 1.1 to 5.0 times as long. It is preferable to use a hot melt adhesive for the attachment means.

Examples of the hot melt adhesive to be used are styrene type hot melt adhesives such as SIS and SBS containing styrene-based block polymers as base polymers; olefin type hot melt adhesives containing amorphous poly($\alpha$-olefins) (APAO) such as ethylene-propylene copolymer and common polyolefin as a base polymer; ethylene-vinyl acetate copolymer (EVA); polyesters; and adhesives containing ethylene-vinyl acetate copolymer as a base polymer. Among them, styrene type hot melt adhesives are preferable. An application method may be contact manner or non-contact manner, however a method in the non-contact application manner (spiral application manner, melt blowing application manner) for applying the adhesive in mesh-like state or spirally applying the adhesive to the fine fibers is preferable in terms of balance between the adhesion strength and softness. The application amount per unit surface area of the hot melt adhesive is preferably about 1 to 10 g/m$^2$.

INDUSTRIAL APPLICABILITY

The absorbent laminate of the invention is made to have the above-mentioned configuration and thus assures a sufficiently high water absorption capability and prevents reversion of the liquid. Further, the upper layer absorbent body contains a large quantity of fibers effective for keeping the form and the width of the opening parts is suppressed to a prescribed level and accordingly, the deformation is hardly caused.

Accordingly, it is made possible to provide economical and disposable absorbent articles free from leakage by disposing the absorbent laminate as an absorbent member for disposable pants, disposable diapers, urine removal pads, sanitary napkins, sanitary shorts, and shorts for light incontinence. Additionally, the absorbent laminate of the invention can be used for not only the disposable absorbent articles but also water-retention and water absorption materials for agriculture; concrete-aging mats; dew formation prevention sheets; wet pad; poultices; and cosmetics.

What is claimed is:

1. An absorbent laminate for absorbing a body fluid and usable for a disposable absorbent article, the absorbent laminate consisting of an upper layer absorbent body, a lower layer absorbent body, an upper layer sheet, and a lower layer sheet, wherein
   the upper layer absorbent body and the lower layer absorbent body are respectively made of fiber aggregates containing 20% by weight or more of highly water-absorbent resin powder,
   the upper layer absorbent body has at least one opening part extended continuously or discontinuously in the longitudinal direction of the upper layer absorbent body,
   the maximum width W1 of the opening part is 40% or less of the minimum width W2 of the upper layer absorbent body,
   the upper layer sheet is disposed on the upper layer absorbent body so as to cover the opening part of the upper layer absorbent body and is bonded to the upper layer absorbent body, and
   the lower layer sheet is folded upward from both side parts of the lower layer absorbent body to the upper face of the lower layer absorbent body, and the lower layer absorbent body is entirely wrapped with the lower layer sheet.

2. The absorbent laminate according to claim 1, wherein the upper layer absorbent body has two or more opening parts which are arranged right and left symmetrically on both sides of the center line along the longitudinal direction of the upper layer absorbent body and has fiber aggregates on the center line along the longitudinal direction of the upper layer absorbent body.

3. The absorbent laminate according to claim 1, wherein the opening part is arranged unevenly in either one of edge sides along the width direction.

4. A disposable absorbent article comprising the absorbent laminate according to claim 1.

5. The absorbent laminate according to claim 1, wherein the lower layer sheet on the top face of the lower layer absorbent body is colored with a color other than white color.

6. The absorbent laminate according to claim 1, wherein the upper layer sheet and the lower layer sheet are hydrophilic or liquid-permeable.

7. The absorbent laminate according to claim 1, wherein one of both of the upper and lower layer sheets and one or both of the upper and lower layer absorbent bodies are bonded.

8. The absorbent laminate according to claim 1, wherein the opening part is arranged unevenly toward a front belly part.

9. The absorbent laminate according to claim 1, wherein:
   the upper layer absorbent body is composed of a single layer, and
   the lower layer absorbent body is composed of another single layer.

10. An absorbent laminate for absorbing a body fluid and usable for a disposable absorbent article, the absorbent laminate consisting of an upper layer absorbent body, a lower layer absorbent body, an upper layer sheet, and a lower layer sheet, wherein
    the upper layer absorbent body is composed of a single layer,
    the lower layer absorbent body is composed of another single layer,
    the upper layer absorbent body and the lower layer absorbent body are respectively made of fiber aggregates containing 20% by weight or more of highly water-absorbent resin powder,
    the upper later absorbent body has at least one opening part extended continuously or discontinuously in the longitudinal direction of the upper later absorbent body,
    the maximum width W1 of the opening part is 40% or less of the minimum width W2 of the upper layer absorbent body,
    the upper layer sheet is disposed on the upper layer absorbent body so as to cover the opening part of the upper layer absorbent body, and
    the lower layer sheet is folded upward from both side parts of the lower layer absorbent body to the upper face of the lower layer absorbent body, and the lower layer absorbent body is entirely wrapped with the lower layer sheet.

11. The absorbent laminate according to claim 10, wherein the upper layer absorbent body has two or more opening parts which are arranged right and left symmetrically on both sides of the center line among the longitudinal direction of the upper later absorbent body and has fiber aggregates on the center line along the longitudinal direction of the upper layer absorbent body.

12. The absorbent laminate according to claim 10, wherein the opening part is arranged unevenly in either one of edge sides along the width direction.

13. A disposable absorbent article comprising the absorbent laminate according to claim 10.

14. The absorbent laminate according to claim 10, wherein the lower layer sheet on the top face of the lower layer absorbent body is colored with a color other than white color.

15. The absorbent laminate according to claim 10, wherein the upper layer sheet and the lower layer sheet are hydrophilic or liquid-permeable.

16. The absorbent laminate according to claim 10, wherein one or both of the upper and lower later sheets and one or both of the upper and lower layer absorbent bodies are bonded.

17. The absorbent laminate according to claim 10, wherein the opening part is arranged unevenly toward a front belly part.

* * * * *